(12) United States Patent
Newkome et al.

(10) Patent No.: US 8,858,832 B2
(45) Date of Patent: Oct. 14, 2014

(54) CONSTRUCTION OF QUANTUM DOTS VIA A REGIOSELECTIVE DENDRITIC FUNCTIONALIZED CELLULOSE TEMPLATE

(75) Inventors: George R. Newkome, Medina, OH (US); Charles N. Moorefield, Akron, OH (US)

(73) Assignee: The University of Akron, Akron, OH (US)

( * ) Notice: Subject to any disclaimer, the term of this patent is extended or adjusted under 35 U.S.C. 154(b) by 761 days.

(21) Appl. No.: 12/301,245

(22) PCT Filed: May 23, 2007

(86) PCT No.: PCT/US2007/069504
§ 371 (c)(1),
(2), (4) Date: Nov. 18, 2008

(87) PCT Pub. No.: WO2008/070199
PCT Pub. Date: Jun. 12, 2008

(65) Prior Publication Data
US 2010/0001235 A1    Jan. 7, 2010

Related U.S. Application Data

(60) Provisional application No. 60/803,004, filed on May 23, 2006.

(51) Int. Cl.
*C12Q 1/68* (2006.01)
*B82Y 10/00* (2011.01)
*B82Y 15/00* (2011.01)
*G01N 33/58* (2006.01)
*H01L 29/12* (2006.01)

(52) U.S. Cl.
CPC .............. *G01N 33/588* (2013.01); *B82Y 10/00* (2013.01); *B82Y 15/00* (2013.01); *H01L 29/127* (2013.01); *Y10S 977/774* (2013.01)
USPC ...................................... 252/301.36; 977/774

(58) Field of Classification Search
USPC ...................................... 977/774; 252/301.36
See application file for complete search history.

(56) References Cited

U.S. PATENT DOCUMENTS

| | | | |
|---|---|---|---|
| 5,731,095 A * | 3/1998 | Milco et al. | 428/482 |
| 6,440,405 B1 | 8/2002 | Cooper et al. | |
| 6,590,056 B2 * | 7/2003 | Won et al. | 528/25 |
| 2003/0018130 A1 | 1/2003 | Dvornic et al. | |
| 2004/0245912 A1 * | 12/2004 | Thurk et al. | 313/484 |
| 2005/0003187 A1 | 1/2005 | Adams et al. | |
| 2005/0058416 A1 | 3/2005 | Hoon Lee et al. | |
| 2005/0059031 A1 | 3/2005 | Bruchez et al. | |
| 2005/0117868 A1 | 6/2005 | Chen et al. | |
| 2005/0176029 A1 | 8/2005 | Heller et al. | |

OTHER PUBLICATIONS

Hassan et al, "Regioselective combinatorial-type synthesis, characterization, and physical properties of dendronized cellulose", Polymer, 46, Aug. 15, 2005, pp. 8947-8955.*

* cited by examiner

*Primary Examiner* — Carol M Koslow
(74) *Attorney, Agent, or Firm* — Renner, Kenner, Greive, Bobak, Taylor & Weber Co., LPA

(57) ABSTRACT

The invention is directed to quantum dot nanoparticles and methods of preparation. Using regioselective dendritic functionalized cellulose, quantum dots may be embedded in the modified cellulosic material. The quantum dot nanoparticles provide use for biotechnology or biomedicinal applications. Photooptical properties and morphology for use in as well as its biocompatibility were investigated.

9 Claims, 5 Drawing Sheets

CONSTRUCTION OF QUANTUM DOTS VIA A REGIOSELECTIVE DENDRITIC FUNCTIONALIZED CELLULOSE TEMPLATE

STATEMENT REGARDING FEDERALLY SPONSORED RESEARCH OR DEVELOPMENT

This invention was made with government support under cooperative agreements awarded by the National Science Foundation (DMR-0196231, DMR-0401780, CHE-0420987), and the Air Force Office of Scientific Research (F49620-02-1-0428,02). The government may have certain rights to the invention.

BACKGROUND OF THE INVENTION

Cellulose is a polydisperse, linear chiral homopolymer consisting of regio- and enantio-selective β-1,4-glycosidic linked D-glucose units. Although it contains three different hydroxyl groups at the C-2, C-3, and C-6 positions, hindered dendrons possessing a focal isocyanate moiety were shown to react exclusively at the primary C-6 positions. Therefore, regioselective functionalization of cellulose, i.e. the introduction of either a substituent or more than one substituent onto the cellulose chain at specific hydroxyl group(s), has lead to precisely modified cellulose materials possessing new properties differing from those derived from simple statistical substitution. Regiocontrol within cellulose chemistry leads to the design of advanced material and nano-scale architectures in interdisciplinary research at the interface of organic and supramolecular chemistry. Utilitarian applications of this chemistry are liquid crystalline polymers, host-guest assemblies, sensor matrices, and bioactive materials.

Semiconductor nanocrystals and quantum dots (QDs) have also received great interest from the biological, medical, electronics and other communities. Compared with conventional organic fluorophores, QDs have high luminescence (1 QD=10 to 20 fluorophores), high resistance to photobleaching, narrow spectral line widths, and tunable emission that can be excited using a single wavelength. However, there are a few major considerations in using these nanoparticles in a biological setting, e.g., the aqueous solubility and biocompatibility required for biological applications.

SUMMARY OF THE INVENTION

The present invention relates to the preparation of stable encapsulated or embedded quantum dots, such as CdS quantum dots, attached to the cellulose main chain, which may be modified by means of the regioselective dendritic functionalization. The photooptical properties as well as morphology are considered.

In an example, the reaction of isocyanate dendrons proceeds regioselectively to functionalize primary alcohol positions and possibly further with secondary and tertiary hydroxyl groups. Treatment of cellulose with the 3rd generation or more isocyanate dendron was demonstrated to regioselectively give the 3rd generation cellulose carbamate at the C-6 hydroxyl groups.

The preparation of CdS quantum dot with {[(HO$_2$C)$_{27}$-Den]-cellulose} is similar to that of the dendrimer-encapsulated nanoparticles as described in co-pending application PCT/US07/69504 filed on an even date herewith, which is incorporated herein by reference. CdS/Cellulose hybrid 3 was prepared by alternating drop-wise addition of Cd$^{2+}$ and S$^{2-}$ [2.0 mM Cd(NO$_3$)$_2$ or 2.0 mM Na$_2$S in MeOH] to a solution (0.12 mM of AUG) containing {[(HO$_2$C)$_{27}$-Den]-cellulose} 2 at 0° C.

DETAILED DESCRIPTION OF THE INVENTION

Figure 1:
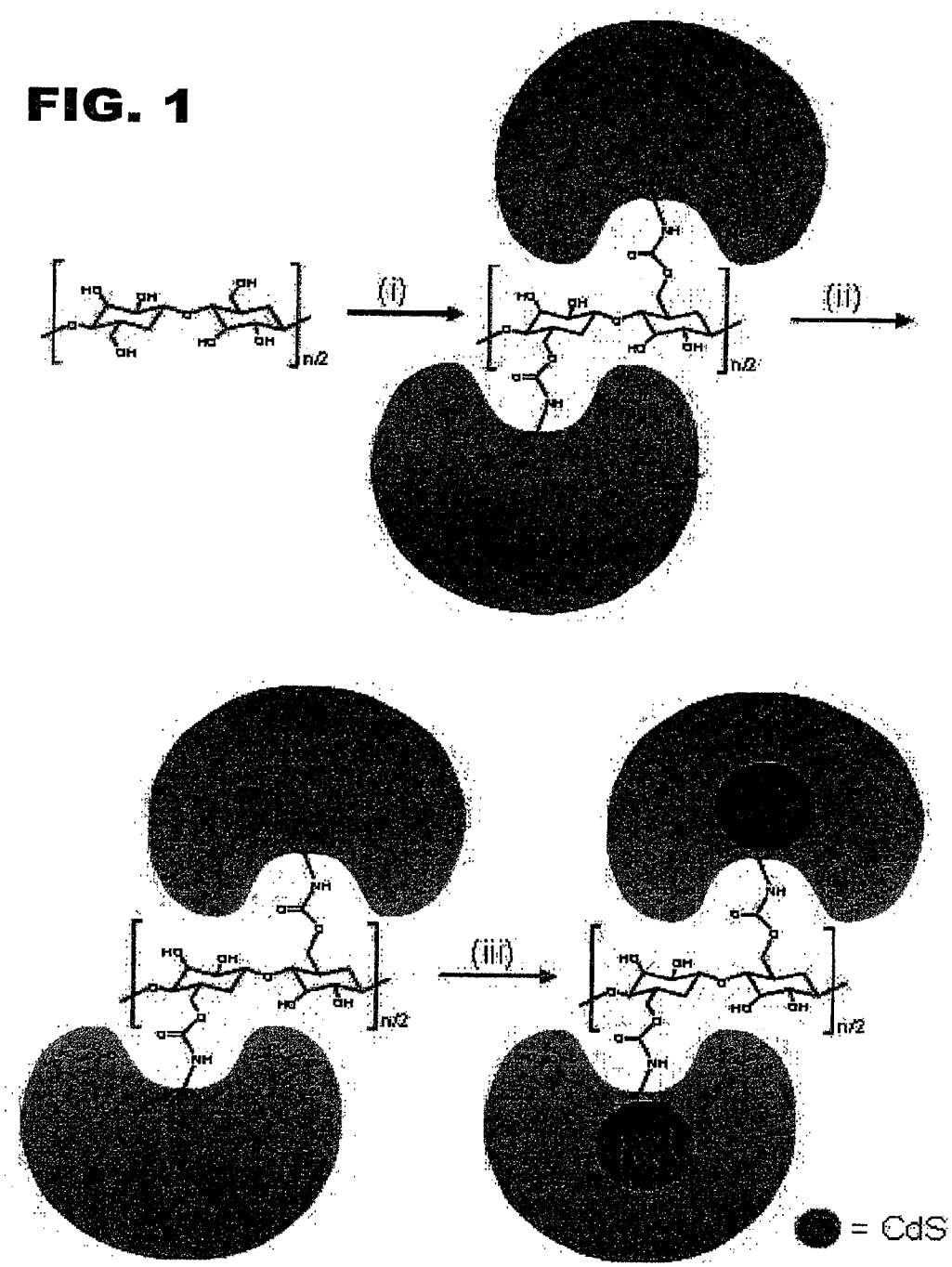
FIG. 1 shows an example of dendronization of a cellulose material to form a nanohybrid composite.

The basic strategy for the preparation of the dendronized cellulose composites with CdS quantum dots is illustrated in FIG. 1. Initially, the dendronized cellulose 1 is formed by reagents and conditions (i) G3-NCO dendron, dibutyltin dilaurate, L1C1, DMAc, 60° C., and the terminal ester groups of the dendronized cellulose 1 were cleaved using formic acid at 25° C. to generate the {[(HO$_2$C)$_{27}$-Den]-cellulose} 2, formed as (ii) HCO$_2$H, 25° C.

Figure 2:
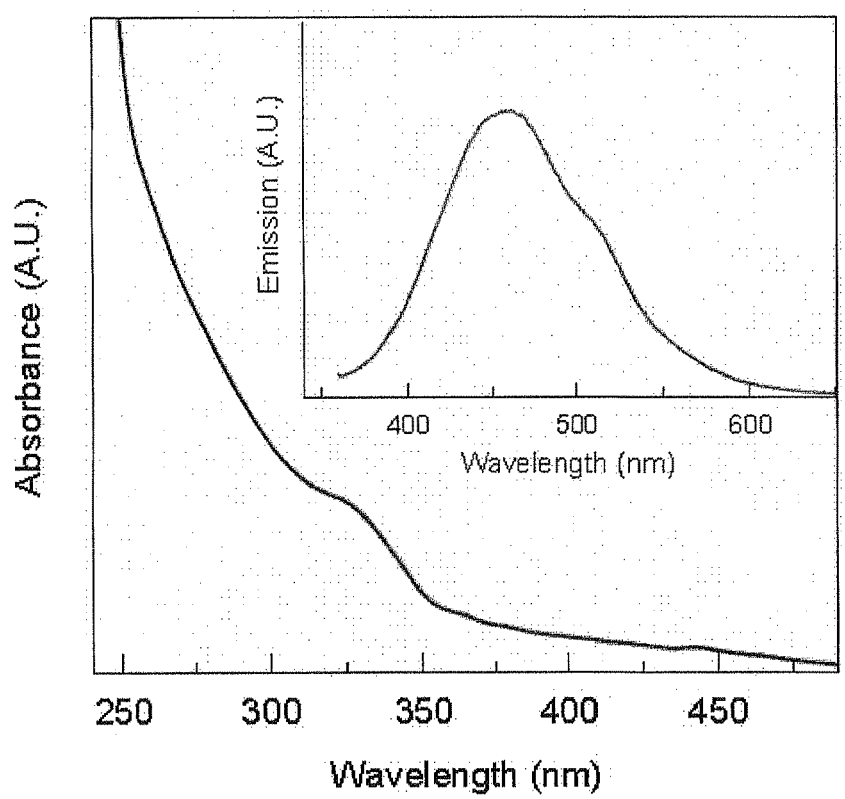
FIG. 2 is a UV/vis absorption spectra and a photoluminescence spectra for CdS/Cellulose hybrid 3.

FIG. 2 shows the absorption and luminescence spectra (inset) for the CdS/cellulose hybrid 3 at 25° C. A significant absorption of UV light at 325 nm (calculated by using Lorentzian multi-peak analysis method) was revealed with a 190 nm blue-shift when compared with the characteristic absorption of the corresponding band-gap of bulk CdS (515 nm), reflecting the quantum confinement effect of the CdS nanocrystal. This corresponds to the first optically allowed transition between the electronic state in the conduction band and the hole state in the valence band. Since the size of the particles is directly related to the absorption wavelength of quantum-sized particles due to size quantization effect, the diameter of the individual CdS particles was predicted to be ca. 2.4 nm from their optical absorbance spectrum. Upon excitation with light at a wavelength of 350 nm, the CdS nanoparticles bound to composite 3 exhibited photo-luminescence with a maximum emission at 459 nm (FIG. 2; inset). This emission peak was assigned to an electron-hole recombination in the CdS nanoparticles and is further indicative of the quantum size effect.

Quantum dots are semiconductive nanocrystals typically between 1 and 10 nanometers in diameter and have unique properties between that of single molecules and bulk materials. Quantum dots offer tunable optical and electronic properties that can work around natural limits inherent in traditional semiconductors. In one aspect of the invention, the quantum dots have a composition that includes cadmium sulfide, cadmium selenide, silicon, germanium or mixtures thereof. In another aspect of the invention, the quantum dots have a heavy metal-free composition that includes indium gallium phosphide. In further aspects of the invention, the quantum dots are uncoated. In particular, the quantum dots may not have a core shell coating, for example zinc sulfide, as used in other available quantum dots.

Figure 3:
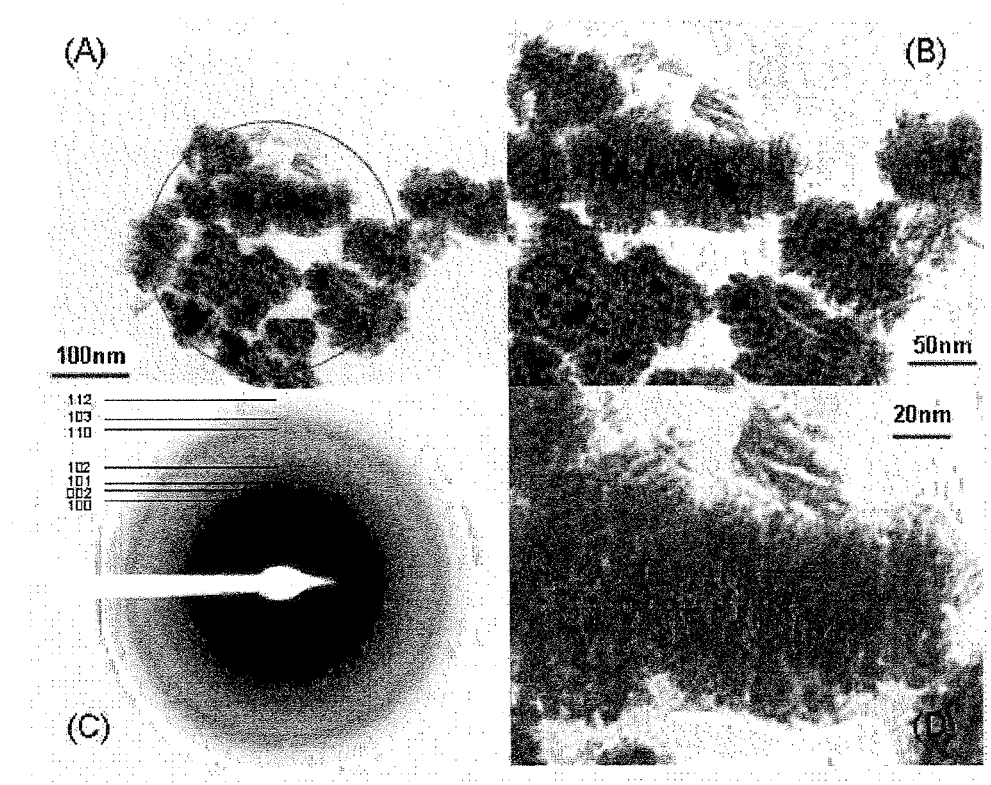
FIG. 3 is a series of transmission electron micrographs for CdS/Cellulose hybrid 3 (A and B) and the selected area electron diffraction pattern taken from the circle in FIG. 2A (C).

FIG. 3 shows a transmission electron microscope (TEM) image of CdS/cellulose hybrid 3 in (A), (B) and (D) taken at 25° C. Although observation of single CdS nanoparticles by TEM was very complicated, it can be seen that the quantum dots layer (dark area in photograph) were packed in an orderly manner. The diameter of dark layer is ca. 3-4 nm; this size is appropriate since the theoretical diameter, based on molecular modeling, for the expended dendron on cellulose main chain (ca. 4.7 nm). FIG. 3(C) shows a selected area electron diffraction (SAED) pattern for the CdS/cellulose hybrid 3 taken from the circular region noted in (A). Calibration of the SAED spacing was conducted using the standard evaporated thallous chloride, which has the largest first-order spacing diffraction of 0.384 nm. Several diffused diffraction rings were revealed with five different d-spacings: 0.358, 0.336, 0.245, 0.207 and 0.176 nm, which belong to Miller indices of the (100), (002), (102), (110) and (112), respectively, for CdS wurtzite; this is in agreement with literature values. This electron diffraction pattern of the CdS at (101) and (103) is very weak, but helps to confirm that the black dot layers of 3 are the randomly oriented, small CdS crystals possessing sizes appropriate for the formed quantum dots.

In one aspect of the invention, treatment of cellulose with the $3^{rd}$ generation isocyanate dendron was demonstrated to regioselectively give the $3^{rd}$ generation cellulose carbamate at the C-6 hydroxyl groups. In another aspect of the invention, at least a $3^{rd}$ generation, and up to a $5^{th}$ generation dendron or more can be porphyrin-based, polyester-based, amino-polyester based, pyridine-based, amide-based or mixtures thereof. In a further aspect of the invention, the dendron is hydrophilic, hydrophobic or mixtures thereof including a hydrophilic outer portion wherein the end groups of the dendron are hydrophilic and a hydrophobic inner portion wherein the core of the dendron is hydrophobic.

Figure 4:
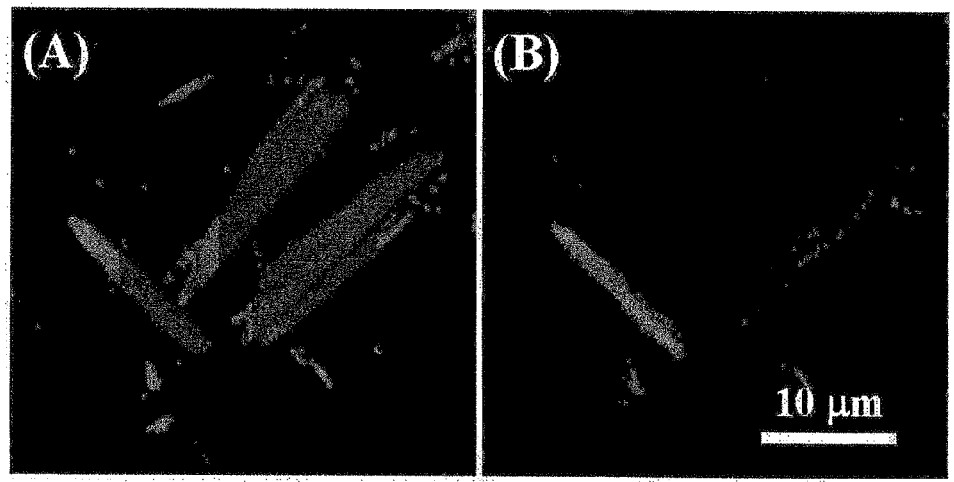
FIG. 4 is pair of a linear polarized optical microscopy (PLM) images without (A) and with (B) a tint retardation plate placed between the analyzer and the sample at room temperature.

To get morphological information on the micro-scale, optical textures at different temperatures were observed with a linear polarized optical microscopy (PLM) coupled with a heating stage. FIG. 4A shows the PLM micrograph of $\{[HO_2C)_{27}\text{-Den}]\text{-cellulose}\}$ 2 at 25° C. Elongated ribbon-like textures were observed against the amorphous background. These textures did not change before the isotropization temperature (157° C.) and subsequent cooling did not give any birefringence suggesting the ribbon-like assemblies were formed in solution. Furthermore, wide angle X-ray diffraction of the $\{[HO_2C)_{27}\text{-Den}]\text{-cellulose}\}$ 2 gave only a diffused amorphous halo in the wide angle region indicating the structure of the birefringent ribbon-like morphology is a mesomorphic liquid crystalline phase. To study the molecular orientation inside the ribbons in FIG. 4A, a tint retardation plate (530 nm) was placed between the sample and the analyzer; as the result is shown in FIG. 4B. All the ribbons going from the upper-left to the lower-right are yellow and all the ribbons going from the upper-right to the lower-left are blue. This indicates that the refractive index perpendicular to the ribbons ($n_⊥$) is higher than the refractive index parallel to the ribbons ($n_∥$). Therefore, the cellulose long axis should align perpendicular to the assembled ribbon-like PLM texture, which agrees well with the TEM result (FIG. 3).

Figure 5:
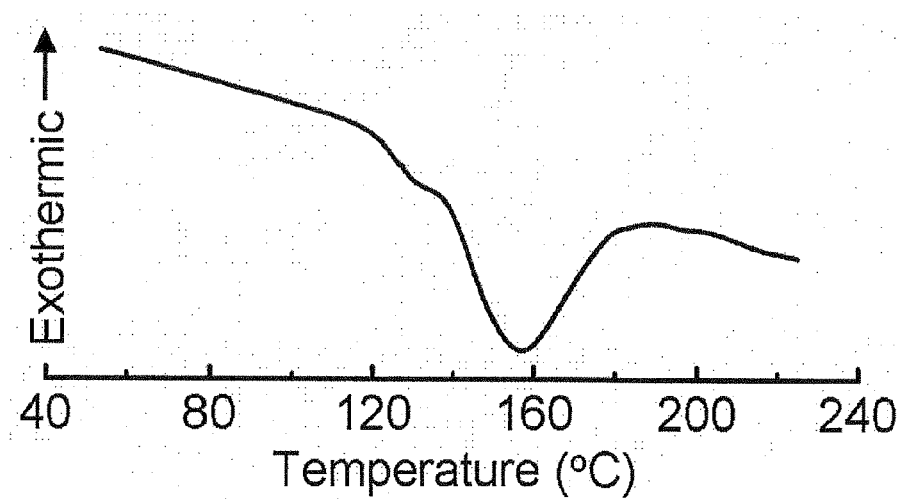
FIG. 5 is a DSC thermogram of the {[HO$_2$C)$_{27}$-Den]-cellulose} 2 at heating rate of 10° C./minute.

No thermal transition was observed during a subsequent cooling and heating (FIG. 5). This further supports the supposition that the ribbon-like assembly was formed in solution.

Figure 6:
FIG. 6 is a photograph of a biocompatibility test for platelets with CdS/cellulose hybrid 3.

It has been suggested that Cd2+ ions released from the surface of Cd-containing nanocrystals are a main cause for the reported toxicity. As a preliminary biocompatiblity test, a procedure wherein platelet-rich plasma is incubated with CdS/cellulose hybrid 3. This simple viability test (see FIG. 6) showed that most platelets were uneffected by the CdS/Cellulose hybrid 3 indicating that the CdS/cellulose hybrid 3 has negligible cytotoxicity due to protection from the dendrons.

Further aspects of the invention include preparing at least $3^{rd}$ generation, and up to $5^{th}$ generation or more dendrons that are used in the preparation of a dendronized substrate including dendronized cellulose. These higher generational dendrons provide additional surface area for embedding higher concentration of quantum dots in the dendronized substrate. A further aspect of the invention includes post-treating the dendronized substrate, wherein the quantum dots are embedded within the dendron, with at least one additional $3^{rd}$ generation, and up to a $5^{th}$ generation dendron or more. Other substrates, including single wall carbon nanotubes, multi-wall carbon nanotubes, polymeric materials, and oligomeric materials, are also envisioned as candidates in the preparation of dendronized substrates.

Based on the foregoing example, it should now be apparent that the present invention provides well-ordered CdS or other quantum dot composite assemblies with dendronized chiral cellulose. The resulting nanohybrids have been characterized by UV/vis, TEM, and SAED; with the size of these QDs appearing to be in the quantum-confined regime and they also exhibit luminescence properties. From the preliminary biocompatibility test, we expect that the CdS quantum dots encapsulated or embedded by dendronized cellulose afford in entrees into molecular biology, biotechnology, and biomedicine.

EXPERIMENTAL SECTION $\{[(HO_2C)_{27}\text{-Den}]\text{-Cellulose}\}$ (2). The dissolution (2.5%) of cellulose in DMAc/LiCl was accomplished as known in the art. To this solution containing 100 mg of cellulose [microcrystalline cellulose, degree-of-polymerization (DP)=280], the $3^{rd}$-generation isocyanate dendron and dibutyltin dilaurate, as catalyst, were added; the ratio of isocyanate to cellulose anhydroglucose unit (AUG) was 3:1 and the catalyst concentration was 2%, base on cellulose. The stirred mixture was maintained at 65° C. for 4 days, after which, the reaction mixture was added to a MeOH/H$_2$O (70:30) solution to yield a precipitate that was next centrifuged, and washed (3×) with a MeOH/H$_2$O mixture. The crude product was purified using dialysis membrane (10,000 MWCO) to remove residual solvent as well as unreacted materials. The solution of modified cellulose 1 (FIG. 1) in formic acid (10 mL) was stirred for 24 h at 25° C. After the reaction, the excess formic acid was removed in vacuo.

Biocompatibility Test. CdS/cellulose hybrid 3 (FIG. 1) coated coverslips were used for the test. Whole blood (9 mL) was drawn from healthy, medication-free human donors into a 10-mL tube containing 1 mL of 3.8% sodium citrate anticoagulant, centrifuged at 800 rpm for 15 min to collect platelet-rich plasma (PRP). The platelet density was about 3.6× $10^5/\mu L$ determined by coulter $A^c$.T diff (Beckman Coulter, Schaumburg, Ill.). The test coverslips were put in a 24-well culture plate and hydrated by adding 500 µL of phosphate buffered saline with calcium and magnesium (PBS) for 15 min, and then they were incubated with 500 µL of diluted PRP with about 3.0×10$^4$ platelets/well for 1 h. The PRP suspension was removed, and the coverslips were gently washed with PBS. Adherent platelets were fixed by adding 500 µL of 1% paraformaldehyde (PFA) in PBS and incubating at 25 ° C. for 1 h, followed by washing with PBS. The coverslips were mounted face-up on a coverslide using Crystal Mount. The images were collected with a Spot RT chilled CCD camera and analyzed using Meta Morph software (Universal Imaging Corp.).

In principle, when platelets die, it is difficult to detect their presence on the microscope slide due to shrinkage. In this test, the platelets and platelet aggregates were observed, and CdS/Cellulose hybrids 3 were also appeared near by platelets, as white spots, on FIG. 6.

What is claimed is:

1. A nanohybrid comprising:
   an isocyanate dendron having a core,
   a quantum dot semiconductive nanocrystal,
   a homopolymeric cellulose material,
   wherein said quantum dot semiconductive nanocrystal is encapsulated or embedded in said dendron,
   wherein a focal moiety connects said cellulose material to said core of said dendron having said quantum dot semiconductive nanocrystal encapsulated or embedded therein.

2. The nanohybrid of claim 1, wherein the quantum dot is uncoated.

3. The nanohybrid of claim 1, wherein the quantum dot comprises cadmium sulfide.

4. The nanohybrid of claim 1, wherein the quantum dot comprises cadmium selenide.

5. The nanohybrid of claim 1, wherein the quantum dot comprises an element taken from the group of silicon and germanium.

6. The nanohybrid of claim 1, wherein the quantum dot comprises indium gallium phosphide.

7. The nanohybrid of claim 1, further comprising a plurality of at least third generation isocyanate dendrons bonded to said cellulose material.

8. The nanohybrid of claim 1, wherein said isocyanate dendron is at least a third generation dendron.

9. The nanohybrid of claim 1, wherein said focal moiety is a carbamate group.

* * * * *